(12) United States Patent
Friedrichs et al.

(10) Patent No.: US 10,537,377 B2
(45) Date of Patent: Jan. 21, 2020

(54) ELECTROSURGICAL GENERATOR WITH HALF-CYCLE POWER REGULATION

(71) Applicant: COVIDIEN LP, Mansfield, MA (US)

(72) Inventors: Daniel A. Friedrichs, Aurora, CO (US); Robert B. Smith, Loveland, CO (US); Steven C. Rupp, Arvada, CO (US)

(73) Assignee: Covidien LP, Mansfield, MA (US)

( * ) Notice: Subject to any disclaimer, the term of this patent is extended or adjusted under 35 U.S.C. 154(b) by 818 days.

(21) Appl. No.: 15/150,466

(22) Filed: May 10, 2016

(65) Prior Publication Data
US 2017/0325872 A1    Nov. 16, 2017

(51) Int. Cl.
*A61B 18/12* (2006.01)
*A61B 17/00* (2006.01)
*A61B 18/00* (2006.01)

(52) U.S. Cl.
CPC .... *A61B 18/1206* (2013.01); *A61B 2017/00141* (2013.01); *A61B 2018/00767* (2013.01); *A61B 2018/1286* (2013.01)

(58) Field of Classification Search
CPC ............ A61B 18/1206; A61B 18/1233; A61B 2018/00726; A61B 2018/00761; A61B 2018/00767; A61B 2018/1286; A61B 2018/1293; A61B 2018/1823; H03F 1/30–303; H03F 1/307; H03F 1/308
See application file for complete search history.

(56) References Cited

U.S. PATENT DOCUMENTS

| 4,727,874 | A |   | 3/1988  | Bowers et al. |
| 5,836,943 | A | * | 11/1998 | Miller, III .......... A61B 18/1206 606/34 |
| 6,979,987 | B2 |  | 12/2005 | Kernahan et al. |
| 8,298,223 | B2 |  | 10/2012 | Wham et al. |
| 9,270,202 | B2 |  | 2/2016  | Johnson et al. |
| 9,379,643 | B2 |  | 6/2016  | Friedrichs et al. |

(Continued)

FOREIGN PATENT DOCUMENTS

| EP | 2777582 A1 | 9/2014 |
| EP | 2826433 A2 | 1/2015 |

(Continued)

OTHER PUBLICATIONS

European Search Report dated Oct. 12, 2017 issued in corresponding European Application No. 17170058.6.

*Primary Examiner* — Jaymi E Della
*Assistant Examiner* — Sean W Collins

(57) ABSTRACT

An electrosurgical generator includes: a power supply configured to output a direct current; an energy metering stage including at least one metering switching component operated by a metering switching waveform, the energy metering stage configured to generate a metered energy packet from the direct current; a power converter coupled to the energy metering stage, the power converter including at least one power switching element operated by a power switching waveform, the power converter configured to generate a radio frequency half cycle based on the metered energy packet; and a controller coupled to the power converter, the controller is configured to modulate the metering switching waveform and the power switching waveform.

17 Claims, 4 Drawing Sheets

(56) References Cited

U.S. PATENT DOCUMENTS

| | | |
|---|---|---|
| 2005/0004564 A1 | 1/2005 | Wham et al. |
| 2005/0143725 A1 | 6/2005 | Daners et al. |
| 2007/0176584 A1 | 8/2007 | Chen |
| 2013/0066311 A1 | 3/2013 | Smith et al. |
| 2014/0254221 A1 | 9/2014 | Johnson et al. |
| 2015/0025523 A1 | 1/2015 | Friedrichs et al. |
| 2015/0032096 A1* | 1/2015 | Johnson ............ A61B 18/1206 606/34 |

FOREIGN PATENT DOCUMENTS

| | | |
|---|---|---|
| WO | 1993003679 A1 | 3/1993 |
| WO | 2009081561 A1 | 7/2009 |
| WO | 2010025807 A1 | 3/2010 |

\* cited by examiner

… (1)

ELECTROSURGICAL GENERATOR WITH HALF-CYCLE POWER REGULATION

BACKGROUND

Technical Field

The present disclosure relates to systems and methods for controlling an electrosurgical generator configured to generate a radio frequency ("RF") waveform having a plurality of RF cycles for treating tissue. In particular, the present disclosure relates to an electrosurgical generator having a power converter and an energy metering stage configured to meter energy into energy packets delivered to the power converter, thereby controlling the RF waveform on a half-cycle basis.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Conventional RF generators may be classified as either voltage-fed sources or current-fed sources. Each of these types of electrosurgical generators generates transients along with RF waveforms. Thus, during short transients, which may be about 1/10th of the length of an RF cycle, a voltage-fed source tends to maintain a fixed voltage, whereas a current-fed source tends to maintain a fixed current. Performance of current-fed or voltage-fed generators is greatly affected by either regular or irregular high-frequency transients. To limit undesired and potentially destructive voltage or current conditions associated with these transients, these power sources may be implemented either as current-limited voltage sources or voltage-limited current sources.

Energy for electrosurgical applications (e.g., vessel sealing) may be provided by either voltage-fed or current-fed sources. However, neither of these designs is optimal for this use. While most of the conventional RF generators have been designed as voltage sources, they require significant modifications to prevent and/or mitigate high-frequency transients, which may interfere with the ability to control power delivery.

Accordingly, there is a need for electrosurgical generator which can deliver energy to tissue at a constant rate, in other words, a generator which inherently behaves as a power source. Thus, there is a need for an RF generator which behaves as a constant energy rate delivery or power source, capable of power regulation on a cycle by cycle basis to respond to high-frequency transients.

SUMMARY

According to one embodiment of the present disclosure an electrosurgical generator is provided. The electrosurgical generator includes: a power supply configured to output a direct current; an energy metering stage including at least one metering switching component operated by a metering switching waveform, the energy metering stage configured to generate a metered energy packet from the direct current; a power converter coupled to the energy metering stage, the power converter including at least one power switching element operated by a power switching waveform, the power converter configured to generate a radio frequency half cycle based on the metered energy packet; and a controller coupled to the power converter, the controller is configured to modulate the metering switching waveform and the power switching waveform.

According to another embodiment of the present disclosure, an electrosurgical generator is provided. The electrosurgical generator includes: a power supply configured to output direct current; an energy metering stage configured to generate a metered energy packet from the direct current; a power converter coupled to the energy metering stage, the power converter including at least one power switching element operated by a power switching waveform, the power converter configured to generate a radio frequency half cycle based on the metered energy packet; and a controller coupled to the power converter, the controller is configured to modulate the power switching waveform.

According to one aspect of any of the above embodiments, the power converter includes four power switching elements arranged in an H-bridge topology.

According to one aspect of any of the above embodiments, the energy metering stage includes a first metering switching element and a second metering switching element, each of which is operated by a metering switching waveform.

According to one aspect of the above embodiment, the controller is coupled to the metering stage, the controller is further configured to modulate the metering switching waveform.

According to one aspect of any of the above embodiments, the electrosurgical generator further includes a pre-regulation stage coupled to the power supply and the energy metering stage, the pre-regulation stage is configured to step down the direct current prior to supplying the direct current to the metering stage.

According to one aspect of any of the above embodiments, the electrosurgical generator further includes at least one sensor coupled to at least one of the power source, the pre-regulation stage, the metering stage, or the power converter, wherein the at least one sensor is configured to measure at least one property of a respective one of the power source, the pre-regulation stage, the metering stage, or the power converter.

According to one aspect of any of the above embodiments, the controller is further configured to modulate at least one of the power switching waveform or the metering switching waveform based on the at least one measured property.

According to a further embodiment of the present disclosure, a method for controlling an electrosurgical generator is provided. The method includes: generating direct current at a power supply; generating a metered packet at an energy metering stage from the direct current; and generating a radio frequency half cycle based on the metered energy packet at a power converter coupled to the energy metering stage.

According to one aspect of the above embodiment, generating the radio frequency half cycle includes activating at least one power switching element of the power converter based on a power switching waveform.

According to one aspect of the above embodiment, generating the metered packet includes activating at least one metering switching element of the energy metering stage based on a metering switching waveform.

According to one aspect of the above embodiment, the method further includes sensing at least one property of the metered packet or the radio frequency half cycle.

According to one aspect of the above embodiment, the method further includes modulating at least one of the power switching waveform or the metering switching waveform based on the at least one sensed property.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that embodiments of the present disclosure may be adapted for use with any electrosurgical instrument. It should also be appreciated that different electrical and mechanical connections and other considerations may apply to each particular type of instrument.

Briefly, an electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various electrosurgical instruments (e.g., monopolar instruments, return electrode pads, bipolar electrosurgical forceps, footswitches, etc.). Further, the generator may include electronic circuitry configured to generate radio frequency energy specifically suited for powering electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
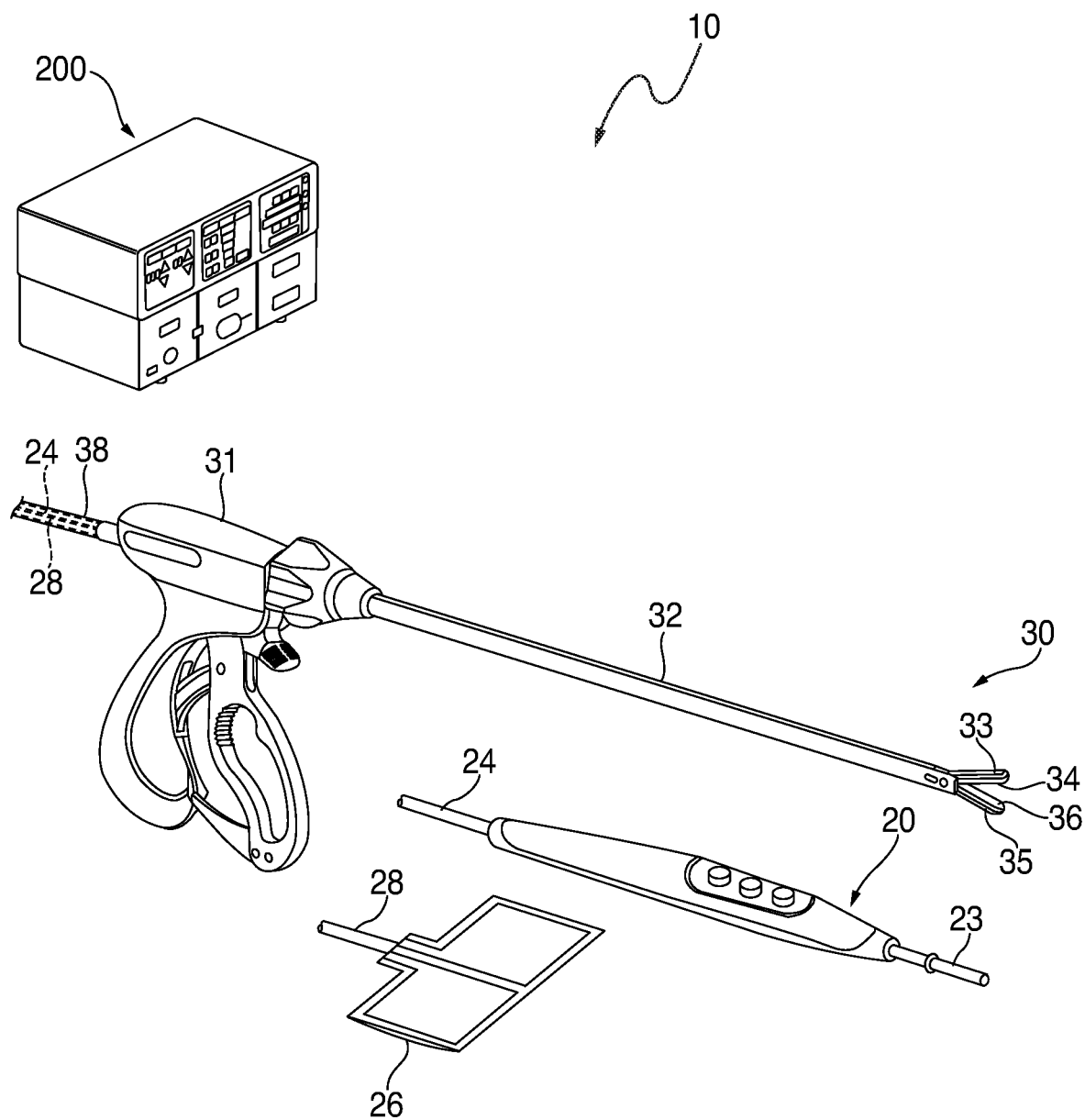
FIG. 1 is a perspective view of an electrosurgical system according to an embodiment of the present disclosure.

Referring to FIG. 1, an electrosurgical system 10 according to the present disclosure includes one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 350 (FIG. 3) of the generator 200, allowing the instrument 20 to cut, coagulate, and/or otherwise treat tissue. The alternating current is returned to the generator 200 through a return electrode pad 26 via a return line 28 at a return terminal 352 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
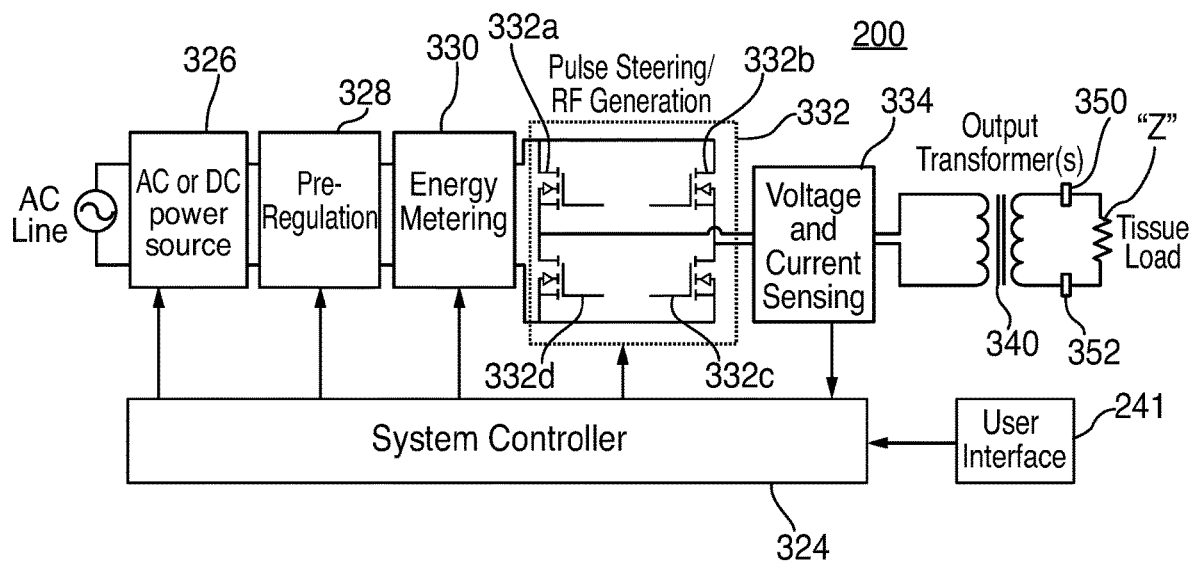
FIG. 3 is a schematic diagram of the electrosurgical generator of FIG. 2 according to an embodiment of the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 350, 352, respectively (FIG. 3). The electrosurgical forceps 30 is coupled to the generator 200 at a port having connections to the active and return terminals 350 and 352 (e.g., pins) via a plug disposed at the end of the cable 38, wherein the plug includes contacts from the supply and return lines 24, 28 as described in more detail below.

Figure 2:
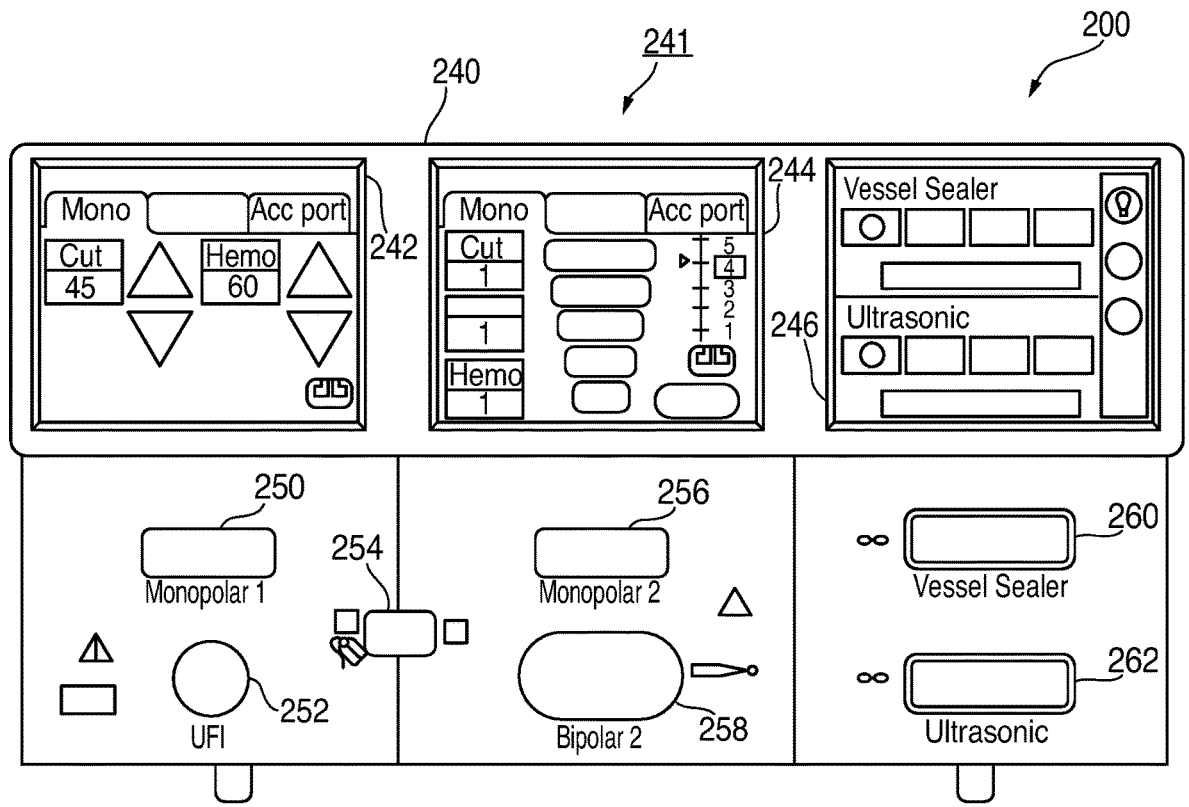
FIG. 2 is a front view of an electrosurgical generator of the electrosurgical system of FIG. 1 according to an embodiment of the present disclosure.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). The port 254 is configured to couple to the return electrode pad 26. Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 324 (FIG. 3) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 350 and 352 may be coupled to any of the desired ports 250-262. In embodiments, the active and return terminals 350 and 352 may be coupled to the ports 250-262.

With reference to FIG. 3, the generator 200 also includes a controller 324, a power supply 326, a pre-regulation stage 328, an energy metering stage 330, and a power converter 332. The power supply 326 may be a high voltage, DC power supply connected to an AC source (e.g., line voltage) and provides high voltage, DC power to the power converter 332, which then converts high voltage, DC power into RF energy and delivers the energy to the active terminal 350. The energy is returned thereto via the return terminal 352. In particular, electrosurgical energy for energizing the monopolar electrosurgical instrument 20 and/or electrosurgical forceps 30 is delivered through the active and return terminals 350 and 352. The active and return terminals 350 and 352 are coupled to the power converter 332 through an isolation transformer 340. The output of power converter 332 transmits current through an isolation transformer 340 to the load "Z", e.g., tissue being treated.

The pre-regulation stage 328 may be a DC-DC buck converter and is coupled to the power supply 326. In embodiments, the pre-regulation stage 328 may be omitted, such that the energy metering stage 330 is directly coupled to the power supply 326. The pre-regulation stage 328 provides finer control of the energy sourced to the load "Z." The pre-regulation stage 328 performs a DC voltage step down or step up conversion and is controlled by the controller 324 prior to supplying energy, i.e., direct current, to the energy metering stage 330.

The power converter 332 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 332 may be a resonant RF amplifier or a non-resonant RF amplifier. A non-resonant RF amplifier, as used herein, denotes an amplifier lacking any tuning components, e.g., conductors, capacitors, etc., disposed between the power converter and the load "Z."

The controller 324 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 324 includes output ports that are operably connected to the power supply 326, the pre-regulation stage 328, the energy meting stage 330, and/or power converter 332 allowing the controller 324 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 324. The controller 324 then controls the power supply 326, the pre-regulation stage 328, the energy meting stage 330, and/or power converter 332, which adjusts power delivered to and/or from the power converter 332, respectively.

The controller 324 may perform various mathematical computations in order to control the power supply 326, the pre-regulation stage 328, the energy meting stage 330, and/or power converter 332 to generate an RF waveform having a desired shape and energy content. Examples of computations performed by the controller 324 include, but are not limited to, calculating instantaneous and/or rms power levels, amount of energy delivered on a cycle by cycle basis, load impedance, etc.

The generator 200 according to the present disclosure may also include a plurality of sensors 334. The sensors 334 are coupled to the power converter 332 and may be configured to sense properties of RF energy outputted by the power converter 332. In embodiments, the generator 200 may also include additional sensor (not shown) coupled to the power supply 326, the pre-regulation stage 328, and/or the energy metering stage 330. The controller 324 also receives input signals from the input controls of the generator 200, the instrument 20 and/or electrosurgical forceps 30. The controller 324 utilizes the input signals to adjust power outputted by the generator 200 and/or performs other control functions thereon.

The power converter 332 includes a plurality of switching elements 332a-332d arranged in an H-bridge topology. In embodiments, power converter 332 may be configured according to any suitable topology including, but not limited to, half-bridge, full-bridge, push-pull, and the like. Suitable switching elements include voltage-controlled devices such as transistors, field-effect transistors (FETs), combinations thereof, and the like.

As described above, the controller 324 is in communication with the power converter 332, in particular, the switching elements 332a-332d. Controller 324 is configured to output a control signal, which may be a pulse-width modulated signal, to switching elements 332a-332d. In particular, controller 324 is configured to modulate a control signal supplied to switching elements 332a-332d of power converter 332. Additionally, controller 324 is configured to calculate power characteristics of generator 200, and control generator 200 based at least in part on the measured power characteristics from the sensors 334.

Figure 4:
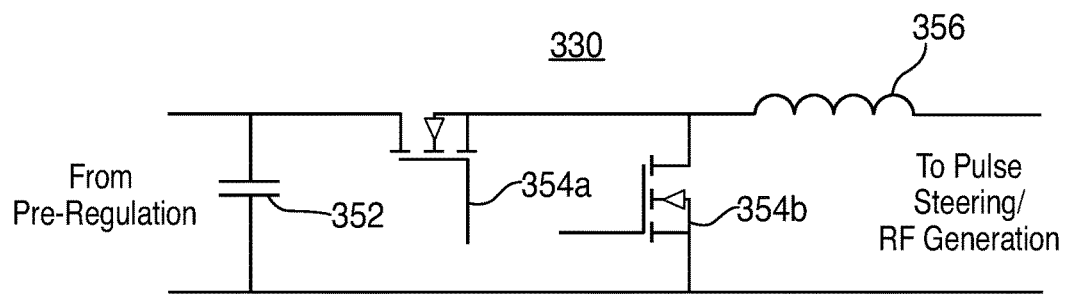
FIG. 4 is a schematic diagram of an energy metering stage of the electrosurgical generator of FIG. 2 according to an embodiment of the present disclosure.

With reference to FIG. 4, the energy metering stage 330 includes a capacitor 352, a first switching element 354a, a second switching element 354b, and an inductor 356. The energy metering stage 330 converts the input power from the pre-regulation stage 328 and/or directly from the power supply 326 into metered energy packets. The first switching element 354a is connected to a ground (not shown) and the second switching element 354b is connected in parallel along with the capacitor 352. The capacitor 352 acts as an input filter to stabilize the voltage feed. The first and second switching elements 354a and 354b are controlled by the controller 324 using a PWM control signal in a push-pull manner. This operation of the first and second switching elements 354a and 354b supplies desired voltage pulses to the inductor 356, which stores the metered pulse energy and supplies the energy to power converter 332. In embodiments, one of the sensors 334 may be coupled to the inductor 356 and configured to monitor current therein.

The power converter 332 receives the metered pulse energy from the energy metering stage 330 and provides a switching and steering path to the load "Z" in the form of a desired RF waveform. The H-bridge configuration of the power converter 332 allows for generation of any suitable waveform, such that polarity can be chosen for each energy pulse. In embodiments, the generated waveform may be an RF waveform including alternating positive and negative pulses. It is envisioned, that the energy metering stage 330 may be configured to generate any arbitrary pulse polarity combination.

Figure 5:
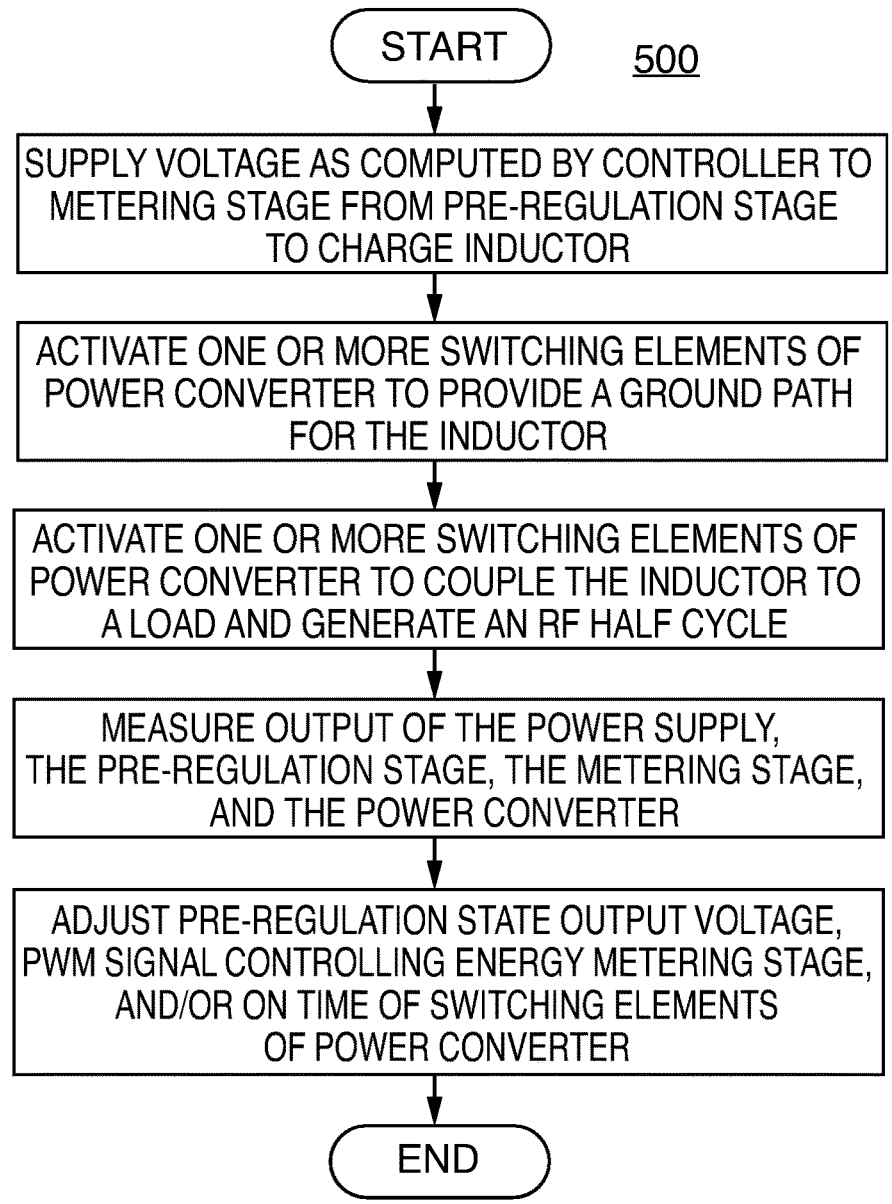
FIG. 5 is a flow chart of a method for operating the electrosurgical generator of FIG. 2 according to an embodiment of the present disclosure.

With reference to FIG. 5, a method 500 for operating the generator 200 to generate an RF waveform 400 (FIG. 6) is shown. For each RF half cycle, the controller 324 sets the voltage at the pre-regulation stage 328 that is to be supplied to the energy metering stage 330.

During each inductor energy charge cycle, an energy pulse having a preset width is applied to the input of the inductor 356. The pulse width is controlled by a PWM control signal supplied to the first and second switching elements 354a and 354b, which may be operated in a push-pull manner to achieve a desired voltage within the inductor 356. In addition, one or more of the switching elements 332a-332d are activated to provide a ground return path for the current built-up in the inductor 356. The voltage is calculated by the controller 224 based on readings from the sensors 334 and/or user input from the user interface 241.

Figure 6:
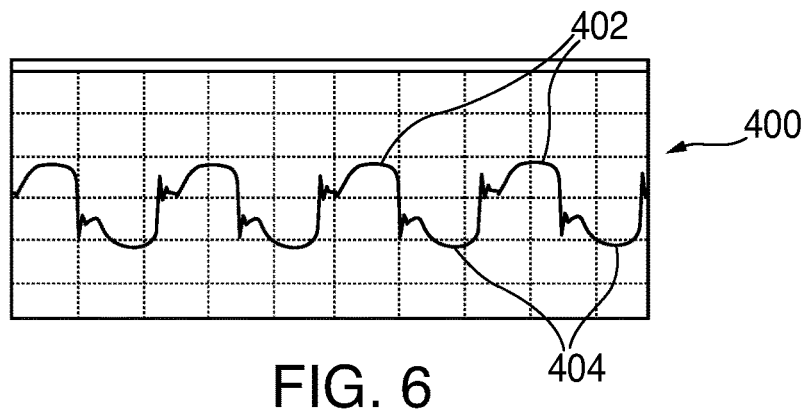
FIG. 6 is a plot of an RF waveform generated by the electrosurgical generator of FIG. 2 according to the present disclosure.

At a predetermined time or once energy within the inductor 356 reaches a predetermined threshold, the inductor 356 is connected to the load "Z" through the power converter 332. One or more of the switching elements 332a-332d are activated to generate either a positive or negative radio frequency half-cycle 402, 404 (FIG. 6) from the energy supplied by the inductor 356. The positive and negative RF half-cycles form the RF waveform 400 as shown in FIG. 6, which is supplied to the load "Z."

During this process, the controller 324 monitors energy parameters of each of the pre-regulation stage 328, the energy metering stage 330, and the power converter 332. Based on the sensed parameters, the controller 324 adjusts output voltage of the pre-regulation 328, adjusts or truncates pulse width of the pulses supplied to the first switching element 354a and/or the second switching element 354b of the energy metering stage, as well as adjusts or truncates the duty cycle and on time of the switching elements 332a-332d of the power converter 332.

These adjustments by the controller 324 allow for generations of many desired wave shapes. FIG. 6 shows an exemplary RF waveform 400 including a plurality of positive RF half cycles 402 and a plurality negative RF half cycles 404. The crest factor, pulse duration, and other properties of the RF waveform 400 may adjusted using the generator 200 according to the present disclosure, in particular, the combined control of the energy metering stage 330 and the power converter 332 by the controller 224 allows for generating the RF waveform 400 having any suitable characteristics.

Although the present disclosure is described with respect to an electrosurgical generator, the embodiments disclosed herein may be utilized in any generator. In particular, the energy metering state according to the present disclosure may be paired with any pulse steering stage (e.g., power converter). In embodiments, the power converter may be configured to generate alternating or direct current waveforms. The combination of the energy metering stage and any suitable power converter allows for fine-tuning of the generated waveform, such as cycle-by-cycle and/or pulse-by-pulse energy control, arbitrary pulse shaping, arbitrary pulse polarity sequencing, arbitrary output frequency control, and instantaneous power delivery monitoring and control.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical generator, comprising:
   a power supply configured to output a direct current;
   an energy metering stage including an inductor, a first metering switching element coupled in series to the inductor and a second metering switching element connected in parallel to the inductor, each of the first metering switching element and the second metering switching element operated by a metering switching waveform, the energy metering stage configured to generate a metered energy packet from the direct current;
   a power converter coupled to the energy metering stage, the power converter including at least one power switching element operated by a power switching waveform, the power converter configured to generate a radio frequency half cycle based on the metered energy packet; and
   a controller coupled to the power converter, the controller is configured to modulate the metering switching waveform and the power switching waveform.

2. The electrosurgical generator according to claim 1, wherein the power converter includes four power switching elements arranged in an H-bridge topology.

3. The electrosurgical generator according to claim 1, further comprising:
   a pre-regulation stage coupled to the power supply and the energy metering stage, the pre-regulation stage configured to step down the direct current prior to supplying the direct current to the energy metering stage.

4. The electrosurgical generator according to claim 3, further comprising at least one sensor coupled to at least one of the power supply, the pre-regulation stage, the energy metering stage, or the power converter, wherein the at least one sensor is configured to measure at least one property of a respective one of the power supply, the pre-regulation stage, the energy metering stage, or the power converter.

5. The electrosurgical generator according to claim 4, wherein the controller is further configured to modulate at least one of the power switching waveform or the metering switching waveform based on the at least one measured property.

6. An electrosurgical generator, comprising:
a power supply configured to output a direct current;
an energy metering stage including an inductor, a first metering switching element coupled in series to the inductor and a second metering switching element connected in parallel to the inductor, the energy metering stage configured to generate a metered energy packet from the direct current;
a power converter coupled to the energy metering stage, the power converter including at least one power switching element operated by a power switching waveform, the power converter configured to generate a radio frequency half cycle based on the metered energy packet; and
a controller coupled to the power converter, the controller is configured to modulate the power switching waveform.

7. The electrosurgical generator according to claim 6, wherein the power converter includes four power switching elements arranged in an H-bridge topology.

8. The electrosurgical generator according to claim 6, wherein each of the first metering switching element and the second metering switching element is operated by a metering switching waveform.

9. The electrosurgical generator according to claim 8, wherein the controller is coupled to the energy metering stage, the controller is further configured to modulate the metering switching waveform.

10. The electrosurgical generator according to claim 8, further comprising:
a pre-regulation stage coupled to the power supply and the energy metering stage, the pre-regulation stage configured to step down the direct current prior to supplying the direct current to the energy metering stage.

11. The electrosurgical generator according to claim 10, further comprising at least one sensor coupled to at least one of the power supply, the pre-regulation stage, the energy metering stage, or the power converter, wherein the at least one sensor is configured to measure at least one property of a respective one of the power supply, the pre-regulation stage, the energy metering stage, or the power converter.

12. The electrosurgical generator according to claim 11, wherein the controller is further configured to modulate at least one of the power switching waveform or the metering switching waveform based on the at least one measured property.

13. A method for controlling an electrosurgical generator, the method comprising:
generating a direct current at a power supply;
generating a metered packet at an energy metering stage from the direct current, the energy metering stage including an inductor, a first metering switching element coupled in series to the inductor and a second metering switching element connected in parallel to the inductor; and
generating a radio frequency half cycle based on the metered energy packet at a power converter coupled to the energy metering stage.

14. The method according to claim 13, wherein generating the radio frequency half cycle includes activating at least one power switching element of the power converter based on a power switching waveform.

15. The method according to claim 14, wherein generating the metered packet includes activating at least one of the first metering switching element or the second metering switching element of the energy metering stage based on a metering switching waveform.

16. The method according to claim 14, further comprising sensing at least one property of the metered packet or the radio frequency half cycle.

17. The method according to claim 16, further comprising modulating at least one of the power switching waveform or the metering switching waveform based on the at least one sensed property.

* * * * *